United States Patent [19]
Voss et al.

[11] Patent Number: 4,690,927
[45] Date of Patent: Sep. 1, 1987

[54] PHARMACEUTICAL COMPOSITIONS WITH ANALGESIC PROPERTIES AND THE PREPARATION AND USE THEREOF

[75] Inventors: Harald Voss, Bad Homburg; Herbert Rothweiler, Rheinfelden-Eichsel, both of Fed. Rep. of Germany

[73] Assignee: Ciba-Geigy Corporation, Ardsley, N.Y.

[21] Appl. No.: 825,293

[22] Filed: Feb. 3, 1986

[30] Foreign Application Priority Data

Feb. 8, 1985 [CH] Switzerland ............... 570/85-4

[51] Int. Cl.$^4$ .............................................. A61K 31/44
[52] U.S. Cl. .................................................... 514/282
[58] Field of Search ........................................ 514/282

[56] References Cited

U.S. PATENT DOCUMENTS

| | | | |
|---|---|---|---|
| 4,126,684 | 11/1978 | Robson et al. | 514/282 |
| 4,234,601 | 11/1980 | Gardocki | 424/319 |
| 4,486,436 | 12/1984 | Sunshine et al. | 514/282 |
| 4,571,400 | 2/1986 | Arnold | 514/282 |

OTHER PUBLICATIONS

Physican's Desk Reference 40th Ed. (1986) pp. 1095, 1096, 1534–1535.
The United States Dispensatory 27th Ed. (1973) p. 331.

Primary Examiner—Stanley J. Friedman
Attorney, Agent, or Firm—Michael W. Glynn; Irving M. Fishman

[57] ABSTRACT

A pharmaceutical composition with analgesic properties which contains a pharmaceutically acceptable salt of diclofenac and a pharmaceutically acceptable salt of codeine in the weight ratio of about 1:1 to 3:1, and the preparation and use thereof.

15 Claims, No Drawings

PHARMACEUTICAL COMPOSITIONS WITH ANALGESIC PROPERTIES AND THE PREPARATION AND USE THEREOF

The present invention relates to pharmaceutical compositions with analgesic properties containing two different drugs with the same properties so as to effect an increase in the desired analgesic effect.

One of the long-existing primary goals of medicine is the relief of pain. Relief is sought usually by the administration of analgesic drugs which increase the pain threshold. It is difficult to satisfy this requirement with a single chemical entity, as a potent analgesic will normally cause concomitant side-effects, whereas a drug that gives rise to few or no side-effects will also generally be a less effective analgesic. Almost all analgesic drugs induce reactions other than the relief of pain. Some of these reactions are e.g. gastrointestinal disorders, dizziness, constipation, nausea, and vomiting. Thus when using analgesics in man, considerations other than achieving the primary effect (amalgesia) must be borne in mind, so that novel drugs are sought which have the maximum analgesic effect accompanied by a minimum of side-reactions. There is therefore a continual search for a combination of drugs which will enable the total amount of drug to be reduced and which can be administered in such proportions that maximum analgesic effect can be produced with little or no side-effects. What is sought is, on the one hand, a potentiation of the therapeutic, i.e. analgesic, effect and, on the other, a reduction of undesirable side-effects. Surprisingly, it has been found that such a potentiating effect is produced by a combination of a pharmaceutically acceptable salt of diclofenac and a pharmaceutically acceptable salt of codeine in the weight ratio of about 1:1 to 3:1, but preferably in the ratio of about 1:1. The onset of activity of the combination of this invention is, surprisingly, as rapid as that of the individual components with longer duration of action. For example, the efficacy of the combination lasts 6 hours longer than that of the individual components, namely diclofenac sodium and codeine phosphate.

Surprisingly, it has also been found that the analgesic effect is significantly better than that of pentazocine, which is subject to control under the law on dangerous drugs. For example, the analgesic activity of a combination comprising 50 mg of diclofenac sodium and 50 mg of codeine phosphate (ratio of 1:1) is significantly better than that of 50 mg of pentazocine and as good as that of 100 mg of pentazocine but with far better tolerance. The effective dosage thereby attainable brings about a reduction of undesirable side-effects.

Both individual components are known substances of the drug armamentarium. Diclofenac [o-(2,6-dichloroanilino)phenylacetic acid], in particular the sodium salt thereof, is used widely in the treatment of inflammatory states by virtue of its antiinflammatory and analgesic properties. The corresponding pharmaceutical compositions are chiefly administered orally and also rectally or parenterally. As a potent analgesic, diclofenac is not always entirely satisfactory when administered in low dosage. Thus oral administration may cause undesirable side-effects in individual patients, especially in the upper region of the gastro-intestinal tract.

Codeine is an analgesic of the opiate type that acts centrally. As regards the possibility of addiction to codeine, it may be inferred from the literature that the danger of habituation may be regarded as slight if the drug is administered in normal oral dosages under medical supervision.

Depending on the dose, the administration of the pharmaceutical compositions of this invention makes it possible to eliminate side-effects very substantially and/or to achieve a more intense therapeutic effect. The compositions of this invention can be used for the treatment of painful conditions.

Suitable dosage unit forms for oral administration are e.g. tablets, layered tablets (tablets with a compressed outer coating), dragées and capsules, which formulations contain 25–150 mg, preferably 50–125 mg, of diclofenac sodium, and 50–75 mg, preferably 50 mg, of codeine phosphate. The ratios of both components should always be within the above indicated range. Suppositories and capsules for rectal administration contain 25–100 mg, preferably 25–75 mg, of diclofenac sodium, and preferably 50 mg of codeine phosphate, while maintaining the ratios indicated above. The dosage unit forms are administered once to three times daily in a quantity corresponding to a daily dose of 75–150 mg of diclofenac sodium and to the single amount to half the amount of codein phosphate for adult patients, whereas reduced doses may be administered to children, depending on age and body weight.

In dosage unit forms for peroral administration, the content of both active components together is preferably from 20 to 90%. To make tablets or dragées cores, the active ingredients are combined e.g. with solid carriers in powder form such as lactose, saccharose, sorbitol or mannitol; starches such as potato starch, corn starch or amylopectin, and also laminaria powder or powdered citrus pulp; cellulose derivatives, gelatin or polyvinylpyrrolidone, without or with the addition of lubricants such as magnesium stearate or calcium stearate, or polyethylene glycols, and with highly dispersed silicic acid. Dragée cores are then coated e.g. with concentrated sugar solutions which may additionally contain gum arabic, talcum and/or titanium dioxide, or with a solution of coating substance in a readily volatile organic solvent or mixture of solvents. Colorants may be added to these coatings, for example to identify or indicate different doses of active ingredient. It is also possible to produce layered tablets by a procedure similar to that employed for making the homogeneous tablets, except that tablet cores are first prepared from only one active component, preferably diclofenac, and then a coating which contains the second component, preferably codeine phosphate, together with the same or similar carriers and lubricants, is compressed onto said cores. Further suitable dosage unit forms for oral administration are two-piece hard gelatin capsules as well as soft elastic capsules made of gelatin and a plasticiser such as glycerol. The hard gelatin capsules preferably contain the active ingredients in granular form together with lubricants and glidants such as talcum or magnesium stearate, and may also contain stabilisers such as sodium metabisulfite ($Na_2S_2O_5$) or ascorbic acid. In soft elastic capsules the active ingedients are preferably suspended in a suitable liquid, e.g. a liquid polyethylene glycol, to which a stabiliser may also be added.

Dosage unit forms for rectal administration are e.g. suppositories that consist of a combination of the active ingredients with a suppository base such as a natural or synthetic triglyceride having a suitable melting point (e.g. cocoa butter), a polyethylene glycol or a suitable higher fatty alcohol; and also gelatin rectal capsules that contain a combination of the active ingredient with a polyethylene glycol.

The following Examples will serve to illustrate the preparation of a number of typical formulations in more detail, without in any way restricting the scope of the invention.

EXAMPLE 1

Preparation of film-coated tablets 200 g of diclofenac sodium and 200 mg of codeine phosphate are thoroughly mixed with 480 g of dicalcium phosphate, 280 g of corn starch and 48 g of colloidal silica. The mixture is spray granulated with a solution of 64 g of hydroxypropyl cellulose (Klucel L ®) in 1216 g of deionised water in a suitable apparatus, and dried. The dried granulate is passed through a 1 mm sieve. Then 225 g of sodium carboxymethyl starch (Primojel), 20 g of colloidal silica and 8 g of magnesium stearate are mixed with the sieved granulate. The mixture is then compressed to tablets weighing 340 mg. The tablets are oblong and have a breaking notch. The tablet cores are then provided with a coating that masks the bitter taste, protects the diclofenac sodium from the action of light and makes the tablets easy to swallow. This is done by coating each tablet with 10 mg of coating substance (enteric-coating) in known manner in a suitable apparatus. To this end, hydroxypropyl methylcellulose (Pharmacoat), polyoxyethylene sorbitan fatty acid ester (Tween), titanium dioxide and talcum are dissolved or suspended in deionised water.

The coated tablet disintegrates rapidly in water or physiological media and releases the active ingredients.

1 Film-coated 350 g tablet contains:
50 mg of diclofenac sodium and
50 mg of codein phosphate.

EXAMPLE 2

Preparation of a drop solution 30 g of diclofenac sodium are dissolved in a solution of 240 g of polyvinylpyrrolidone (Kollidon) in 1035 g of 1,2-propylene glycol. Then 30 g of codeine phosphate are dissolved in 159 g of deionised water. The two solutions are combined. Saccharine sodium, sodium cyclamate and aromatic substances are added to improve the flavour. The final solution is filled into small brown glass bottles.

2.32 ml of drop solution contains:
50 mg of diclofenac sodium and
50 mg of codeine phosphate.

EXAMPLE 3

Preparation of suppositories

Micronised diclofenac sodium and codeine phosphate are suspended in fused suppository base material (hard fat, Ph. Eur. Vol. III, with a hydroxyl number <5). Fat-soluble colorants (e.g. chlorophyll) or coloured pigments may be added. The suspension is cast in known manner in moulds. These moulds have either been preformed from plastics material and serve as packaging after heat-sealing or they are made of metal. After they have cooled, the suppositories are removed from the moulds and heat-sealed in foil. The suppositories are usually torpedo-shaped, white or coloured, and weight about 2 g. When administered rectally, the suppositories melt and release the active ingredients.

1 Suppository contains:
50 mg of diclofenac sodium and
50 mg of codeine phosphate.

What is claimed is:

1. A pharmaceutical composition having analgesic properties comprising a pharmaceutically acceptable salt of diclophenac and a pharmaceutically acceptable salt of codeine in a weight ratio of about 1:1 to about 3:1.

2. The composition of claim 1 wherein said pharmaceutically acceptable salt of diclophenac is diclophenac sodium and said pharmaceutically acceptable salt of codeine is codeine phosphate.

3. A pharmaceutical composition having analgesic properties comprising diclophenac sodium and codeine phosphate in a weight ratio of about 1:1.

4. The composition of claim 1 which is in unit dose form.

5. The composition of claim 3 which is in unit dose form.

6. The composition of claim 4 wherein said unit dose form is a tablet, a capsule, a suppository, or a drop solution.

7. The composition of claim 5 wherein said unit dose form is a tablet, a capsule, a suppository, or a drop solution.

8. A process for the preparation of the composition of claim 4 comprising intimately mixing an effective antinociceptive amount of pharmaceutically acceptable salt of pharmaceutically acceptable salt of diclofenac and a pharmaceutically acceptable salt of codeine in a weight ratio of about 1:1 to about 3:1.

9. The process of claim 8 wherein said pharmaceutically acceptable salt of diclophenac is diclofenac sodium and said pharmaceutically acceptable salt of codeine is codeine phosphate.

10. A process for the preparation of the composition of claim 5 comprising mixing an effective antinociceptive amount of diclofenac sodium and codeine phosphate in a weight ratio of about 1:1.

11. A process of claim 8 wherein said unit dosage form is a tablet, a capsule, a suppository, or a drop solution.

12. The process of claim 9 wherein said unit dosage form is a tablet, a capsule, a suppository, or a drop solution.

13. The process fo claim 10 wherein said unit dosage form is a tablet, a capsule, a suppository or a drop solution.

14. An analgesic treatment comprising administering to a patient an effective analgesic amount of a composition according to claim 1.

15. An analgesic treatment comprising administering to a patient an effective analgesic amount of a composition of claim 3.

* * * * *